United States Patent
Lombardo et al.

(10) Patent No.: US 10,774,289 B2
(45) Date of Patent: Sep. 15, 2020

(54) FRAGRANCE MATERIAL

(71) Applicant: TAKASAGO INTERNATIONAL CORPORATION, Tokyo (JP)

(72) Inventors: Louis J. Lombardo, Washingtonville, NY (US); Michael E. Lankin, High Bridge, NJ (US); Frank Derosa, Chelmsford, MA (US); Maureen Blandino, Dumont, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 16/099,767

(22) PCT Filed: Jun. 8, 2017

(86) PCT No.: PCT/US2017/036627
§ 371 (c)(1),
(2) Date: Nov. 8, 2018

(87) PCT Pub. No.: WO2017/214446
PCT Pub. Date: Dec. 14, 2017

(65) Prior Publication Data
US 2019/0177653 A1    Jun. 13, 2019

Related U.S. Application Data

(60) Provisional application No. 62/347,327, filed on Jun. 8, 2016.

(51) Int. Cl.
| | | |
|---|---|---|
| C11D 3/50 | (2006.01) |
| C11B 9/00 | (2006.01) |
| A61K 8/33 | (2006.01) |
| A61Q 5/02 | (2006.01) |
| A61Q 15/00 | (2006.01) |
| A61K 8/40 | (2006.01) |
| A23L 2/56 | (2006.01) |
| A61Q 19/00 | (2006.01) |
| A61Q 19/10 | (2006.01) |
| A61Q 5/12 | (2006.01) |
| A23L 27/00 | (2016.01) |
| A23L 27/20 | (2016.01) |
| C11D 3/395 | (2006.01) |

(52) U.S. Cl.
CPC .............. *C11B 9/0015* (2013.01); *A23L 2/56* (2013.01); *A23L 27/202* (2016.08); *A23L 27/88* (2016.08); *A61K 8/33* (2013.01); *A61K 8/40* (2013.01); *A61Q 5/02* (2013.01); *A61Q 5/12* (2013.01); *A61Q 15/00* (2013.01); *A61Q 19/00* (2013.01); *A61Q 19/10* (2013.01); *C11D 3/3953* (2013.01); *C11D 3/50* (2013.01); *A23V 2002/00* (2013.01)

(58) Field of Classification Search
CPC ...... A23L 27/2024; C11B 9/0015; C11D 3/50
See application file for complete search history.

(56) References Cited

U.S. PATENT DOCUMENTS

| | | | |
|---|---|---|---|
| 3,463,818 A | 8/1969 | Blumenthal | |
| 4,420,423 A | 12/1983 | Boden et al. | |
| 4,515,711 A | 5/1985 | Chalk et al. | |
| 5,089,162 A * | 2/1992 | Rapisarda | C11D 3/40 252/187.24 |
| 2005/0145711 A1* | 7/2005 | Blondeau | A61L 9/12 239/60 |
| 2007/0149424 A1* | 6/2007 | Warr | A61Q 13/00 510/101 |
| 2008/0139378 A1* | 6/2008 | Hildebrand | A01K 1/0152 502/1 |
| 2008/0319088 A1 | 12/2008 | Smith | |
| 2009/0202652 A1* | 8/2009 | Stowell | C07C 45/68 424/497 |
| 2010/0087351 A1 | 4/2010 | Fadel et al. | |
| 2010/0099594 A1* | 4/2010 | Bobnock | C11D 3/505 510/119 |
| 2010/0216679 A1* | 8/2010 | Batchelor | C11D 3/507 510/107 |
| 2013/0011353 A1 | 1/2013 | Rautenstrauch et al. | |
| 2015/0118174 A1 | 4/2015 | Ueda et al. | |

FOREIGN PATENT DOCUMENTS

| | | | |
|---|---|---|---|
| GB | 2528480 | * | 1/2016 |
| WO | WO 2014/056848 A1 | | 4/2014 |

OTHER PUBLICATIONS

International Search Report dated Sep. 1, 2017 in International Application No. PCT/US17/36627.
Database PubChem Compound [Online] Feb. 12, 2015 (Feb. 12, 2015), "2-Methyl-4-prop-2-enoxypentane," XP002797005, retrieved from National Center for Biotechnology Information Database accession No. CID=87170260 *abstract.
Hoepfner et al., "Synthese Und Riechstoff-Eigenschften Von Rosenoxid-Analoga," Liebigs Ann Chem, pp. 99-113 (1986) (with English abstract).
Luyben et al., "Design and Control of the Methoxy-Methyl-Heptane Process," Industrial and Engineering Chemistry Research 49:6164-6175 (2010).
Supplemental European Search Report dated Jan. 31, 2020 in Application No. EP 17811039.

* cited by examiner

*Primary Examiner* — John R Hardee
(74) *Attorney, Agent, or Firm* — Baker Botts L.L.P.

(57) ABSTRACT

Fragrance compounds having a unique chemical structure are provided, including 2-methoxy-2-methylheptane and derivatives thereof. The fragrance compounds can have fruity, radish, and/or herbaceous odor notes with a strong top note. The fragrance compounds can be used alone or incorporated into a fragrance composition and/or consumer product to modify or enhance the odor of the fragrance composition and/or consumer product.

16 Claims, No Drawings

FRAGRANCE MATERIAL

CROSS-REFERENCE TO RELATED APPLICATIONS

This application is a U.S. National Stage Patent Application under 35 U.S.C. § 371 of International Application No. PCT/US2017/036627, filed on Jun. 8, 2017, which claims priority to U.S. Provisional Application No. 62/347,327 filed Jun. 8, 2016, the contents of each of which are is hereby incorporated by reference in their its entirety.

FIELD

The presently disclosed subject matter relates to chemical compositions useful as fragrance compounds in fragrance compositions.

BACKGROUND

The fragrance industry is constantly reliant on the development of new chemicals with favorable organoleptic properties. Such new fragrance compounds can be used to create new fragrance compositions having unique odor characteristics or can modify or enhance the organoleptic properties of existing fragrance compositions. Fragrance compositions are used in a wide variety of consumer products, including fine fragrances, personal care products, home care products, air care products, and the like.

Differences in chemical structures can significantly impact odor, notes, and other organoleptic, chemical, and physical characteristics. Thus, there is a continuous need for new chemical structures that have favorable organoleptic properties. Once identified, these novel chemical compounds can provide perfumers and other persons with the ability to create new, unique fragrances.

The presently disclosed subject matter addresses these and other needs by providing a new fragrance compound with unique and desirable organoleptic properties, as discussed in detail below.

SUMMARY OF THE INVENTION

The present disclosure provides fragrance compounds having fruity, radish, and/or herbaceous odor notes with a strong top note. These compounds can be used alone or incorporated into a fragrance composition and/or consumer product.

In certain aspects, the present disclosure provides a fragrance composition comprising a fragrance compound of Formula I or an isomer thereof:

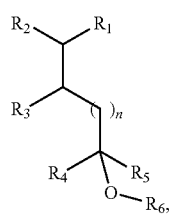

(I)

wherein $R_1$ is selected from isobutenyl or a C1-C6 branched or straight-chain alkyl group;

$R_2$ is selected from H and methyl;

$R_3$ is selected from H and methyl;

$R_4$ is selected from H and a C1-C4 branched or straight-chain alkyl group;

$R_5$ is selected from H and a C1-C4 branched or straight-chain alkyl group;

$R_6$ is selected from H and a C1-C6 branched or straight-chain alkyl or alkenyl group; and n is an integer selected from 0, 1, 2, and 3.

In certain embodiments, $R_1$ is selected from methyl, butyl, and isobutenyl; $R_2$ is selected from H and methyl; $R_3$ is H; $R_4$ is selected from H and methyl; $R_5$ is selected from methyl and isobutyl; $R_6$ is selected from methyl and a C3-C5 alkenyl group; and n is selected from 0, 1, and 2. For example and not limitation, the C3-C5 alkenyl group is selected from allyl, methallyl, and prenyl.

In certain embodiments, the fragrance compound is selected from the group consisting of 2-methoxy-2-methylheptane; 7-methoxy-2,4-dimethyloct-2-ene; 7-methoxy-2,4,7-trimethyloct-2-ene; 7-(allyloxy)-2,4-dimethyloct-2-ene; 7-methoxy-2,4-dimethyloctane; 4-(allyloxy)-2,6-dimethylheptane; 2,6-dimethyl-4-((2-methylallyl)oxy)heptane; 4-methoxy-2,6-dimethylheptane; 2-methyl-4-((2-methylallyl)oxy)pentane; 2-(allyloxy)-4-methylpentane; 2-methyl-4-((3-methylbut-2-en-1-yl)oxy)pentane; isomers thereof; and combinations thereof. In particular embodiments, the fragrance compound is 2-methoxy-2-methylheptane.

As embodied herein, the fragrance composition can further include an additional fragrance compound selected from a citrus compound, a floral compound, a fruity compound, a gourmand compound, a green compound, a musk compound, a spicy compound, a woody compound, and combinations thereof. In certain embodiments, the fragrance composition can further include a solvent.

In certain aspects, the present disclosure also provides methods of modifying the odor properties of a fragrance composition by adding to the fragrance composition an olfactory effective quantity of a fragrance compound of Formula I. For example, the fragrance compound can be 2-methoxy-2-methylheptane.

In certain other aspects, the present disclosure provides a consumer product comprising a consumer product base and a fragrance compound of Formula I, or an isomer thereof. The fragrance compound can be selected from the group consisting of 2-methoxy-2-methylheptane; 7-methoxy-2,4-dimethyloct-2-ene; 7-methoxy-2,4,7-trimethyloct-2-ene; 7-(allyloxy)-2,4-dimethyloct-2-ene; 7-methoxy-2,4-dimethyloctane; 4-(allyloxy)-2,6-dimethylheptane; 2,6-dimethyl-4-((2-methylallyl)oxy)heptane; 4-methoxy-2,6-dimethylheptane; 2-methyl-4-((2-methylallyl)oxy)pentane; 2-(allyloxy)-4-methylpentane; 2-methyl-4-((3-methylbut-2-en-1-yl)oxy)pentane; isomers thereof; and combinations thereof. For example, the fragrance compound can be 2-methoxy-2-methylheptane.

In certain embodiments, the consumer product is selected from a fine fragrance, a personal care product, a home care product, and an air care product. For example, the fine fragrance can be selected from parfum, extrait de parfum, eau de parfum, millesime, parfum de toilette, eau de toilette, eau de cologne, body splash, after shave, body mists, and baby colognes. The personal care product can be selected from lotions, creams, moisturizers, body washes, hand soaps, shampoos, conditioners, and soaps. The home care product can be selected from fabric conditioner, fabric softener, laundry detergent, laundry additive, rinse additive, bleach, dryer sheets, perfume beads, car care products, dishwashing detergent, and hard surface cleaners. The air care product can be selected from a candle, aerosol, air freshener, liquid electric air freshener, fragrance diffuser, gel air freshener, plug-in air freshener, plug-in oil, and wax melt.

The present disclosure also provides methods of modifying the odor properties of a consumer product by adding to a consumer product base an olfactory effective quantity of a fragrance compound of Formula I, or an isomer thereof.

In certain other aspects, the present disclosure provides methods of manufacturing a consumer product comprising admixing a fragrance compound of Formula I, or an isomer thereof, with a consumer product base. In certain embodiments, the fragrance compound is incorporated into a fragrance composition prior to admixing with the consumer product base.

In additional aspects, the present disclosure provides novel fragrance compounds, including 7-methoxy-2,4-dimethyloct-2-ene; 7-methoxy-2,4,7-trimethyloct-2-ene; 7-(allyloxy)-2,4-dimethyloct-2-ene; 7-methoxy-2,4-dimethyloctane; 4-(allyloxy)-2,6-dimethylheptane; 2,6-dimethyl-4-((2-methylallyl)oxy)heptane; 2-methyl-4-((2-methylallyl)oxy)pentane; 2-(allyloxy)-4-methylpentane; 2-methyl-4-((3-methylbut-2-en-1-yl)oxy)pentane; and isomers thereof.

The foregoing has outlined broadly the features and technical advantages of the present application in order that the detailed description that follows can be better understood. Additional features and advantages of the application will be described hereinafter which form the subject of the claims of the application. It should be appreciated by those skilled in the art that the conception and specific embodiment disclosed can be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

DETAILED DESCRIPTION

As noted above, to date, there remains a need in the art for fragrance compounds having improved organoleptic properties. Additionally, there remains a need for fragrance compositions and consumer products comprising such fragrance compounds.

The present disclosure relates to compounds of Formula I, or an isomer thereof:

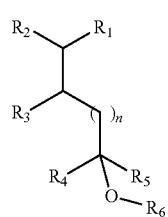

(I)

in which $R_1$ is a group represented by isobutenyl or a C1-C6 branched or straight-chain alkyl group;

$R_2$ is H or methyl;

$R_3$ is H or methyl;

$R_4$ is H or a C1-C4 branched or straight-chain alkyl group;

$R_5$ is H or a C1-C4 branched or straight-chain alkyl group;

$R_6$ is H or a C1-C6 branched or straight-chain alkyl or alkenyl group; and n is an integer from 0 to 3.

The present disclosure also provides isomers, including stereoisomers, diastereoisomers, and enantiomers, of compounds according to Formula I.

For example, compounds according to Formula I include, but are not limited to, 2-methoxy-2-methylheptane, 7-methoxy-2,4-dimethyloct-2-ene, 7-methoxy-2,4,7-trimethyloct-2-ene, 7-(allyloxy)-2,4-dimethyloct-2-ene, 7-methoxy-2,4-dimethyloctane, 4-(allyloxy)-2,6-dimethylheptane, 2,6-dimethyl-4-((2-methylallyl)oxy)heptane, 4-methoxy-2,6-dimethylheptane, 2-methyl-4-((2-methylallyl)oxy)pentane, 2-(allyloxy)-4-methylpentane, 2-methyl-4-((3-methylbut-2-en-1-yl)oxy)pentane and isomers, stereoisomers, diastereoisomers, and enantiomers thereof, and combinations thereof. In particular embodiments, the fragrance compound is 2-methoxy-2-methylheptane or a derivative thereof.

The presently disclosed compounds can have fruity, radish, and/or herbaceous odor notes with a strong top note. These compounds can be used alone or incorporated into a fragrance composition to modify or enhance the odor of existing fragrance compositions, solvents, media, consumer products, and the like.

1. Definitions

The terms used in this specification generally have their ordinary meanings in the art, within the context of this disclosed subject matter and in the specific context where each term is used. Certain terms are discussed below, or elsewhere in the specification, to provide additional guidance to the practitioner in describing the compositions and methods of the disclosed subject matter and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "weight percent" or "wt-%" is meant to refer to the quantity by weight of a component in a material as a percentage of the total wet weight of the material (i.e., a fragrance formulation). Unless otherwise specified, all amounts expressed as a percentage herein represent the amount in weight percent.

The terms "fragrance composition", "fragrance", "fragrance formulation", "perfume" and "perfume composition" mean the same to refer to a perfumed composition that is a mixture of fragrance compounds including for example, alcohols, aldehydes, ketones, esters, ethers, acetates, nitriles, terpene hydrocarbons, nitrogenous or sulphurous heterocyclic compounds and essential oils of natural or synthetic origin, which are admixed so that the combined odors of the individual components produce a pleasant or desired fragrance. Many of these ingredients are listed in reference texts such as S. Arctander, Perfume and Flavor Chemicals, 1969, Montclair, N.J., USA (or any of its more recent versions), which is herein incorporated by reference in its entirety. As described herein, fragrance compositions can be a mixture of any number of fragrance compounds. For example, fragrance compositions include "simple accords", e.g., having fewer than 10 fragrance compounds, and "complex fragrances", e.g., having more than 30 fragrance compounds. In certain embodiments, the fragrance compositions of the present disclosure can be a combination of 2 or more accords.

As used herein, the term "improving" is understood to mean raising a fragrance composition to a more desirable character, the term "enhancing" is understood to mean making the fragrance composition greater in effectiveness, such as strength, and the term "modifying" is understood to mean providing the fragrance composition with a change in character.

As used herein, the term "isomers" refers to different compounds that have the same molecular formula but differ in arrangement and configuration of the atoms. Also as used herein, the term "stereoisomer" refers to any of the various stereo isomeric configurations which may exist for a given compound of the presently disclosed subject matter and includes geometric isomers. It is understood that a substituent may be attached at a chiral center of a carbon atom. Therefore, the presently disclosed subject matter includes enantiomers, diastereomers or racemates of the compound. Also as used herein, the terms "constitutional isomers" refers to different compounds which have the same numbers of, and types of, atoms but the atoms are connected differently.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro or levorotatory) which they rotate plane polarized light at the wavelength of the sodium D line. The compounds of the presently disclosed subject matter contain one or more asymmetric centers and may thus give rise to enantiomers, diastereomers, and other stereoisomeric forms that may be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

2. Methods of Making a Fragrance Compound

Fragrance compounds of Formula I can be prepared according to procedures known in the art. By way of a non-limiting example, fragrance compounds of Formula I can be prepared from an ester starting material. Reacting the ester with a Grignard reagent and a subsequent aqueous acidic workup can produce a tertiary alcohol. The Grignard reagent can be prepared according to procedures as known in the art and can preferably be an alkyl magnesium halide, such as an alkyl magnesium bromide. Preferably the Grignard reaction is carried out at a molar ratio of at least 2 moles of the Grignard reagent for each one mole of ester. A dehydration reaction of the tertiary alcohol product of the Grignard reaction can be carried out by heating in the presence of acid to produce an alkene. An addition reaction of alkene with an alcohol can result in a fragrance compound of Formula I. For example and not limitation, this addition reaction can be carried out according to procedures known in the art, e.g., by treatment with a strong acid or by oxymercuration. For purposes of illustration, this method is described in Example 1, wherein the initial ester is ethyl caproate, the Grignard reagent is methylmagnesium bromide, the tertiary alcohol is 2-hydroxy-2-methylheptane, the alkene is a mixture of 2-methyl-1-heptene and 2-methyl-2-heptene, and the final fragrance compound is 2-methoxy-2-methylheptane.

By means of another non-limiting example, fragrance compounds of Formula I can also be prepared from an alcohol starting material. Deprotonation can be carried out according to procedures known in the art to produce an alkoxide. Preferably, the deprotonation is carried out by a strong base, such as sodium hydride. This alkoxide can undergo a nucleophilic substitution reaction to produce a fragrance compound of Formula I. Preferably, the nucleophilic substitution is carried out on an alkyl halide, such as an alkyl iodide or an alkyl bromide, wherein the halogen is the leaving group in the substitution reaction. This method is illustrated in Examples 4 through 13. In Example 4, the alcohol starting material is 5,7-dimethyloct-6-en-2-ol, the alkyl halide is methyl iodide, and the final fragrance compound is 7-methoxy-2,4-dimethyloct-2-ene.

3. Fragrance Compounds

The present disclosure provides fragrance compounds that are able to impart a fruity, radish, and/or herbaceous odor and that have a strong top note. For example, and not limitation, the fragrance compounds can have the structure according to Formula I, below:

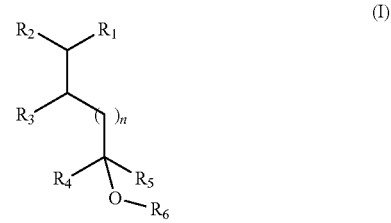

in which $R_1$ is a group represented by X or a C1-C6 branched or straight-chain alkyl group;

$R_2$ is H or methyl;

$R_3$ is H or methyl;

$R_4$ is H or a C1-C4 branched or straight-chain alkyl group;

$R_5$ is H or a C1-C4 branched or straight-chain alkyl group;

$R_6$ is H or a C1-C6 branched or straight-chain alkyl or alkenyl group;

n is an integer from 0 to 3; and

X is isobutenyl, as shown in Formula II, below:

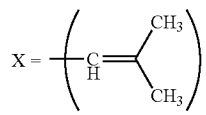

In certain embodiments, the fragrance compound can be an isomer, stereoisomer, diastereoisomer, or enantiomer of a compound according to Formula I.

The fragrance compounds of the present disclosure can impart a number of different odors, including for example and not limitation, one or more apple, bitter green, cheesy, cilantro, coriander leaf, dirty, earthy, fatty, floral, fresh, fruity, green, green apple, herbaceous, hyacinth, mushroom, natural, minty, pear, radish, sharp fruity, sour, spicy, sweet, and/or tomato odors.

In certain embodiments, $R_1$ is methyl, isobutyl, or isobutenyl; $R_2$ is H or methyl; $R_3$ is H; $R_4$ is H or methyl; $R_5$ is methyl or isobutyl; $R_6$ is methyl or a C3-C5 alkenyl group; and n is 0, 1, or 2. In certain embodiments, the C3-C5 alkenyl group can be allyl, methallyl, or prenyl.

In particular embodiments, $R_1$ is methyl; $R_2$ is H; $R_3$ is H; $R_4$ is methyl; $R_5$ is methyl; $R_6$ is methyl; and n is 2. For example, such a fragrance compound can be 2-methoxy-2-methylheptane, or an isomer, stereoisomer, diastereoisomer, or enantiomer thereof. Such a fragrance compound can have a spicy, fresh, green, and/or fruity odor.

In other particular embodiments, $R_1$ is isobutenyl; $R_2$ is methyl; $R_3$ is H; $R_4$ is H; $R_5$ is methyl; $R_6$ is methyl; and n is 1. For example, such a fragrance compound can be 7-methoxy-2,4-dimethyloct-2-ene, or an isomer, stereoisomer, diastereoisomer, or enantiomer thereof. Such a fragrance compound can have a bitter green, minty, and/or fruity odor.

In other particular embodiments, $R_1$ is isobutenyl; $R_2$ is methyl; $R_3$ is H; $R_4$ is methyl; $R_5$ is methyl; $R_6$ is methyl; and n is 1. For example, such a fragrance compound can be 7-methoxy-2,4,7-trimethyloct-2-ene, or an isomer, stereoisomer, diastereoisomer, or enantiomer thereof. Such a fragrance compound can have a weak green odor.

In other particular embodiments, $R_1$ is isobutenyl; $R_2$ is methyl; $R_3$ is H; $R_4$ is H; $R_5$ is methyl; $R_6$ is allyl (i.e., a C3 alkenyl); and n is 1. For example, such a fragrance compound can be 7-(allyloxy)-2,4-dimethyloct-2-ene, or an isomer, stereoisomer, diastereoisomer, or enantiomer thereof. Such a fragrance compound can have a natural fresh, earthy, and/or mushroom odor.

In other particular embodiments, $R_1$ is isobutyl; $R_2$ is methyl; $R_3$ is H; $R_4$ is H; $R_5$ is methyl; $R_6$ is methyl; and n is 1. For example, such a fragrance compound can be 7-methoxy-2,4-dimethyloctane, or an isomer, stereoisomer, diastereoisomer, or enantiomer thereof. Such a fragrance compound can have a green apple note with a floral hyacinth odor.

In other particular embodiments, $R_1$ is methyl; $R_2$ is methyl; $R_3$ is H; $R_4$ is H; $R_5$ is isobutyl; $R_6$ is allyl (i.e., a C3 alkenyl); and n is 0. For example, such a fragrance compound can be 4-(allyloxy)-2,6-dimethylheptane, or an isomer, stereoisomer, diastereoisomer, or enantiomer thereof. Such a fragrance compound can have a fatty, green, tomato, coriander leaf, and/or cilantro odor.

In other particular embodiments, $R_1$ is methyl; $R_2$ is methyl; $R_3$ is H; $R_4$ is H; $R_5$ is isobutyl; $R_6$ is methallyl (i.e., a C4 alkenyl); and n is 0. For example, such a fragrance compound can be 2,6-dimethyl-4-((2-methylallyl)oxy)heptane, or an isomer, stereoisomer, diastereoisomer, or enantiomer thereof. Such a fragrance compound can have a fruity odor.

In other particular embodiments, $R_1$ is methyl; $R_2$ is methyl; $R_3$ is H; $R_4$ is H; $R_5$ is isobutyl; $R_6$ is methyl; and n is 0. For example, such a fragrance compound can be 4-methoxy-2,6-dimethylheptane, or an isomer, stereoisomer, diastereoisomer, or enantiomer thereof. Such a fragrance compound can have a sharp fruity and/or apple odor.

In other particular embodiments, $R_1$ is methyl; $R_2$ is methyl; $R_3$ is H; $R_4$ is H; $R_5$ is methyl; $R_6$ is methallyl (i.e., a C4 alkenyl); and n is 0. For example, such a fragrance compound can be 2-methyl-4-((2-methylallyl)oxy)pentane, or an isomer, stereoisomer, diastereoisomer, or enantiomer thereof. Such a fragrance compound can have a sweet, fruity, and/or pear odor.

In other particular embodiments, $R_1$ is methyl; $R_2$ is methyl; $R_3$ is H; $R_4$ is H; $R_5$ is methyl; $R_6$ is allyl (i.e., a C3 alkenyl); and n is 0. For example, such a fragrance compound can be 2-(allyloxy)-4-methylpentane, or an isomer, stereoisomer, diastereoisomer, or enantiomer thereof. Such a fragrance compound can have a dirty and/or minty odor.

In other particular embodiments, $R_1$ is methyl; $R_2$ is methyl; $R_3$ is H; $R_4$ is H; $R_5$ is methyl; $R_6$ is prenyl (i.e., a C5 alkenyl); and n is 0. For example, such a fragrance compound can be 2-methyl-4-((3-methylbut-2-en-1-yl)oxy)pentane, or an isomer, stereoisomer, diastereoisomer, or enantiomer thereof. Such a fragrance compound can have a sour and/or cheesy odor.

In addition to the fragrance compounds described generally and specifically herein, the present disclosure also includes isomers, such as stereoisomers, diastereoisomers, and enantiomers, thereof.

4. Fragrance Compositions

The fragrance compounds of the presently disclosed subject matter can be formulated into different fragrance compositions. For example, a fragrance composition in accordance with the presently disclosed subject matter can include one or more, two or more, or three or more of the fragrance compounds described above.

Formulations of fragrance compounds into fragrance compositions span the range from "simple accords" (<10 fragrance compounds) to "complex fragrances" (>30 fragrance compounds). For example, full bodied fragrance compositions generally do not comprise less than about 30 fragrance compounds. Such fragrance compositions can also contain or consist of at least one fragrance base, solvent, or combination thereof. Said fragrance bases or solvents may be a liquid or a solid and typically do not significantly alter the olfactory properties of the fragrance compounds.

Some non-limiting examples of fragrance bases include an emulsifying system, encapsulating materials, natural or modified starches, polymers, gums, pectins, gelatinous or porous cellular materials, and waxes.

Some non-limiting examples of solvents include diproplyene glycol, propylene glycol, dieth-phthalate (DEP), diisononyl phthalate (DINP), benzyl benzoate, benzyl alcohol, iso propyl myristate (IPM), isopropyl palmitate (IPP/Deltyl Prime), butyl stearate, dioctyl adipate, triethyl citrate, methyl hydrogenated rosinate (CAS No. 8050-15-5), terpenes (e.g., Glidsol 100), paraffinic naphthenic solvent (e.g., LPA-170 Solvent), isoalkanes (e.g., Soltrol 170 Isoparaffin), isoparaffins, isooctadecanol, (e.g., Tego Alkanol 66), phenoxyethanol, diethylene glycol monoethyl ether (Carbitol low gravity), glycol ether (Methyl Carbitol), Dipropylene Glycol Methyl Ether (e.g., Dowanol DPM), Dipropylene Glycol Methyl Ether Acetate (e.g., Dowanol DPMA), Propylene glycol methyl ether (e.g., Dowanol PM Glycol Ether), Tripropylene Glycol Methyl Ether, Diisoheptyl Phthalate (e.g., Jayflex® 77 available from Exxon), deionized or distilled water, specially denatured ethyl alcohol (e.g., SDA 40B), Dimethyl Adipate/Dimethyl Glutarate (e.g., DBE®-LVP Esters available from FLEXISOLV®), Racemic mixture (+/−)-2,2-dimethyl-4-hydroxymethyl-1,3-dioxolane (e.g., Augo Clean Multi Solvent), Alcohol 40B Anhydrous 200 Proof, alcohol SDA 40B 190 Proof, Triacetin, 3-Methoxy-3-methyl-1-butanol (Solfit), Benzyl Laurate, Tripropylene Glycol Methyl Ether (e.g., Dowanol TPM), Dipropylene glycol n-butyl ether (e.g., Dowanol DPNB), Dimethyl siloxane, trimethylsiloxy-terminated (e.g., Dowanol Corning 200 Fluid), Caprylic/Capric Triglycerides (e.g., Neobee M-5), propylene glycol and glyceryl oleate (e.g., Arlacel 186), Uniceth-IC20L (e.g., Arlasolve 200 L), propanediol, 1, 3, Butyl Cellosolve, Hexylene glycol, Glycerine, N Methyl Stearate, Isopropyl alcohol, 2-Methyl-1,3-propanediol (e.g., MP Diol Glycol), Diethyl Citrate, Triethyl Acetyl Citrate, Isopentyldiacetate (IPD-AC, Dimethyl 2-methylpentanedioate (e.g., Rhodiasolv Iris), medium chain triglicyrides (MTC), terpene hydrocarbons (e.g., Dipentene 5100, DL-limonene (e.g., Dipentene 122), 3,5,5-trimethylhexyl acetate, Diethyl Malonate, Limonene (e.g., Unitene D), cyclohexyl acetate, para-tertiary-butyl (e.g., Vertenex), Ethyl Acetate, Diethyl Succinate, and natural solvents including, but not limited to, vegetable oils, such as sunflower oil.

The amount of the fragrance compound of Formula I present in a fragrance composition will depend on the formulation, but the compound of the present disclosure is typically present in an amount of from about 0.00001% to about 30.0% by weight of the total fragrance composition. Typically a more preferred embodiment would contain between about 0.01% and about 20% by weight and a most preferred embodiment would contain between about 0.01% and about 10% by weight.

In certain embodiments, the one or more fragrance compounds of the present disclosure are formulated in a fragrance composition in amounts of from about 0.01% to about 99% by weight of the total fragrance composition, or from about 0.01% to about 90% by weight, or from about 0.01% to about 80% by weight, or from about 0.01% to about 70% by weight, or from about 0.01% to about 60% by weight, or from about 0.01% to about 50% by weight, or from about 0.01% to about 40% by weight, or from about 0.01% to about 30% by weight, or from about 0.01% to about 20% by weight, or from about 0.01% to about 10% by weight, or from about 0.02% to about 10% by weight, or from about 0.05% to about 10% by weight, or from about 0.1% to about 10% by weight, or from about 0.1% to about 5% by weight, or from about 0.5% to about 2% by weight, or about 1% of the total fragrance composition. In certain embodiments, the fragrance compositions of the present disclosure contain at least about 0.0001% by weight. For example, at a concentration of at least about 0.0001% by weight of the fragrance composition, some odor notes of the fragrance compounds can be detected. In certain embodiments, the fragrance compositions of the present disclosure contain at least about 0.1% by weight, or at least about 0.5% by weight. In more preferred embodiments, the fragrance compositions of the present disclosure contain at least about 1% by weight. For example, at a concentration of at least about 1% by weight of the fragrance composition, the full character of the fragrance compounds can be detected.

In certain embodiments, the fragrance compositions of the present disclosure contain at least about 98.5% by weight of a fragrance compound, e.g., a compound of Formula I. In one embodiment, the fragrance composition contains 100% by weight of a fragrance compound, e.g., a compound of Formula I.

In certain embodiments, the fragrance compound is 2-methoxy-2-methylheptane, 7-methoxy-2,4-dimethyloct-2-ene, 7-methoxy-2,4,7-trimethyloct-2-ene, 7-(allyloxy)-2,4-dimethyloct-2-ene, 7-methoxy-2,4-dimethyloctane, 4-(allyloxy)-2,6-dimethylheptane, 2,6-dimethyl-4-((2-methylallyl)oxy)heptane, 4-methoxy-2,6-dimethylheptane, 2-methyl-4-((2-methylallyl)oxy)pentane, 2-(allyloxy)-4-methylpentane, 2-methyl-4-((3-methylbut-2-en-1-yl)oxy)pentane, or an isomer, stereoisomer, diastereoisomer, or enantiomer thereof, or a combination thereof. In particular embodiments, the fragrance compound is 2-methoxy-2-methylheptane or a derivative thereof.

A fragrance composition can further include one or more additional fragrance accords or compounds. In certain embodiments, the additional fragrance accords or compounds can be but are not limited to, one or more aldehydic compound(s), one or more balsamic compound(s), one or more citrus compound(s), one or more floral compound(s), one or more fruity compound(s), one or more gourmand compound(s), one or more green compound(s), one or more marine compound(s), one or more mossy compound(s), one or more musk compound(s), one or more piney compound(s), one or more powdery compound(s), one or more spicy compound(s), and/or one or more woody compound(s), or combinations thereof.

For example and not limitation, an aldehydic compound can be aldehyde c-12 MNA. A balsamic compound can be isopropoxy ethyl salicylate and/or benzy salicylate. A citrus compound can be citral, citronellal, L-citronellol, decanal, limonene, myrcenol, nootkatone, sinensal, bergamot oil, grapefruit oil, lemon oil, lime oil, and/or orange oil. A floral compound can be anisyl acetate, anisic aldehyde, benzyl acetate, bourgeonal, butyl acetate, cyclamen aldehyde, cyclohexyl lactone, δ-damascone, farnesal, L-famesal, famesol, florhydral, floralozone, geraniol, gemayl acetate, piperonal, hedione, heliobouquet, hexyl cinnamaldehyde, hexyl salicylate, indole, α-ionone, β-ionone, isopropoxy ethyl salicylate, jasmodione, cis-jasmone, kovanol, laurinol, linalool, linalyl acetate, mayol, methyl dihydrojasomante, γ-methyl ionone, methoxymelonal, nerol, nerolione, neryl acetate, 2-pentyl cyclopentanone, phenoxanol, phenoxy ethyl isobutyrate, phenylacetaldehyde, phenyl ethyl alcohol, rose oxide, suzaral, undecavertol, geranium oil, lavender oil, rose oil, and/or ylang oil. A fruity compound can be aldehyde C-C16, allyl caproate, allyl cyclohexyl proprionate, allyl heptanoate, amyl acetate, benzaldehyde, L-citronellyl acetate, L-citronellyl nitrile, cyclacet, damascenone, 3-decalactone, γ-decalactone, diethyl malonate, dimethyl phenyl ethyl carbinol, dimethyl sulfide, γ-dodecalactone, ethyl acetate, ethyl butyrate, ethyl caproate, ethyl decadienotate, ethyl-2-methylbutyrate, ethyl acetoacetate, ethyl propionate, florol, hexyl acetate, hexyl isobutyrate, isoamyl acetate, jasmolactone, manzanate, melonal, methyl heptyl ketone, γ-nonalactone, γ-octalactone, phenyl ethyl isobutyrate, raspberry ketone, ringonol, thesaron, tolyl aldehyde, γ-undecalactone, vanoris, and/or verdox. A gourmand compound can be caprylic acid, coumarin, ethyl fraison, ethyl vanillin, ethyl maltol (e.g., Veltol Plus), filbertone, furaneol, guaiacol, maple furanone, 2-acetyl pyrazine, 2,5-dimethyl pyrazine, and/or vanillin. A green compound can be dynascone, galbanolene, trans-2-hexenal, cis-3-hexenol, hexen-1-ol, cis-3-hexenyl acetate, cis-3-hexenyl butyrate, cis-3-hexenyl salicyclate, liffarome, methyl octine carbonate, 2,6-nonadienal, oxane, stemone, styrallyl acetate, triplal, undecavertol, violet methyl carbonate (e.g., violet T), vionil, and/or violet leaf extract. A marine compound can be myrac aldehyde and/or Calone 1951. A mossy compound can be oakmoss #1. A musk compound can be ambrettolide, ambretone, ambroxan, exaltolide, galaxolide, habanolide, helvetolide, (1'R)-3-methyl-5-(2,2,3-trimethylcyclopentan-1-yl)-2-pentanone, muscenone, musk T, L-muscone, and/or tonalid. A piney compound can be β-pinene. A powdery compound can be heliotropine and/or whiskey lactone (methyl octalactone). A spicy compound can be β-caryophellene, cinnamaldehyde, cuminaldehyde, eugenol, isoeugenol, perilla aldehyde, cardamom oil, clove oil, ginger extract and/or black pepper extract. A woody compound can be amber core, amber extreme, ambroxan, bacdanol, cedramber, cedanol, ebanol, hindinol, hinokitiol, javanol, norlimbanol dextro, osyrol, patchone, polyambrol, α-pinene, β-pinene, sandalmysore core, sandalore, santalex T, orbitone, cedarwood oil, patchouli oil, sandalwood oil, and/or vetiver oil.

In certain embodiments, the additional fragrance compounds are formulated in a composition in an amount of from about 0.001% to about 99% by weight, or from about 0.01% to about 90% by weight, or from about 0.1% to about 80% by weight, or from about 1% to about 70% by weight, or from about 2% to about 60% by weight, or from about 5% to about 50% by weight, or from about 10% to about 40% by weight, or from about 15% to about 30% by weight, or from about 20% to about 25% by weight.

In certain aspects, the present disclosure provides methods to modify, enhance, or improve the odor properties of a fragrance composition by adding an olfactory effective quantity of the compounds of the present disclosure, e.g., a compound of Formula I, to the fragrance composition. As used herein, the term "olfactory effective quantity" means the amount of said compound in a fragrance composition in which the individual component will contribute its characteristic olfactory properties, for example an olfactory property found to be more hedonically appealing. A person of ordinary skill in the art may optimize the olfactory effect of the fragrance composition based on the incorporation of a fragrance compound of the present disclosure. The fragrance compound may be used individually, or a part of mixture such that the sum of the effects of all fragrance ingredients present in the mixture yields a higher hedonistic rating. Therefore, the compound embodied in the present disclosure can be employed to modify the characteristics of existing fragrance composition via their own olfactory properties or through additively effecting the contributions of other ingredient(s) present within the said composition. The quantity will vary widely depending on the other ingredients present, their relative amounts, the desired effect and the nature of the product.

5. Consumer Products

In certain embodiments, the fragrance compounds and compositions of the present disclosure can be formulated as part of a consumer product. For example and not limitation, the fragrance compounds and/or compositions can be used in perfumes, colognes, shampoos, rinses, skin cares, body shampoos, body rinses, body powders, air fresheners, deodorants, baths, foods, snacks, beverages, and the like, if necessary in combination with auxiliary materials.

As embodied herein, a compound of Formula I can be employed alone or incorporated into fragrance compositions, which can advantageously be used in a wide variety of consumer products. For example, the consumer products can be those intended to perfume a suitable substrate. As used herein, the term "substrate" means any surface to which the consumer product can be applied without causing any undue adverse effect. The substrate can be a wide range of materials including human or animal skin or hair, paper (e.g., fragranced paper), air in a room, fabric, furnishings, dishes, hard surfaces, and related materials. Thus, substrates can include body surfaces such as, for example, hair and skin.

For example, the present disclosure provides a consumer product comprising: (a) at least one compound of Formula I; and (b) a consumer product base. As used herein, "consumer product base" means a composition for use as a consumer product to fulfill the specific purpose of the consumer product, such as cleaning, softening, and caring or the like. The present disclosure also provides a method for improving, enhancing, or modifying a consumer product base by adding thereto an olfactory effective amount of at least one compound of Formula I.

The compound described herein may be employed in a consumer product base simply by directly mixing at least one compound of Formula I, or a fragrance composition comprising at least one compound of Formula I, with the consumer product base, or the compound described herein can, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or it can be chemically bonded to substrates, which are adapted to release the fragrance molecule upon application of an external stimulus such as light, enzymes, or the like, and then mixed with the consumer product base. Thus, the present disclosure additionally provides a method of manufacturing a perfumed consumer product, comprising incorporating a compound of Formula I, as a fragrance ingredient, either by directly admixing the compound to the consumer product base or by admixing a fragrance composition comprising a compound of Formula I with a consumer product base. Admixing can be performed using conventional techniques and methods. Through the addition of an olfactory effective amount of at least one compound of the present disclosure, the odor notes of a consumer product base can be improved, enhanced, or modified. For example, the consumer product base can be modified to improve or enhance a fruity, radish, or herbaceous odor note.

In certain embodiments, the consumer products of the present disclosure can be, but are not limited to, air care products (e.g., candles, aerosols, air fresheners, liquid electric air fresheners, fragrance diffusers, gel air fresheners, plug-in air fresheners and oils, wax melts, etc.); baby care products (e.g., consumer products relating to disposable absorbent and/or non-absorbent articles, including adult incontinence garments, bibs, diapers, training pants, infant and toddler care wipes; and personal care products including hand soaps, shampoos, lotions, shower gels, and clothing); fabric and home care products (e.g., consumer products for fabric conditioning (including softening), laundry detergency, laundry and rinse additive and/or care, bleach, dryer sheets, perfume beads, air care, car care, dishwashing, hard surface cleaning and/or treatment, and other cleaning for consumer and or institutional use, etc.); personal care products (e.g., lotions, creams, moisturizers, body washes, hand soaps, shampoos, conditioners, soaps, etc.); family care products (e.g., wet or dry bath tissue, facial tissue, disposable handkerchiefs, disposable towels, and/or wipes, towels, toilet paper, tissue paper, wet towels, etc.); feminine care products (e.g., catamenial pads, incontinence pads, interlabial pads, panty liners, pessaries, sanitary napkins, tampons and tampon applicators, and/or wipes, etc.); sexual health care products (e.g., products relating to sexual aids or sexual health, including lubricants and condoms, etc.); pet care products (e.g., pet malodor cat litter, pet deodorizers, pet health and nutrition including pet foods, treats, other orally deliverable products, grooming aids, products for treating pet hair/fur including shampooing, styling, conditioning; deodorants and antiperspirants; products for cleansing or treating pet skin, including soaps, creams, lotions, and other topically applied products; training aids, toys and diagnostics techniques); fine fragrance (including hydro alcoholic solutions of perfume oil, such as parfum, extrait de parfum, eau de parfum, millesime, parfum de toilette, eau de toilette, eau de cologne, body splash, after shave, body mists, including baby colognes); auto care products (e.g., cleaners, air fresheners, wipes, soaps, etc.); cosmetics (e.g., skin cream, cleansing cream, night cream, hand cream, lotion, after-shave lotion, body lotion, foundation, lip stick, lip cream, nail polish, nail polish remover, talcum powder, anti-wrinkle and/or anti-aging cosmetics, sun protection products, massage oil, etc.); beauty care (e.g., products for treating human hair including shampooing, styling, conditioning; deodorants and antiperspirants; products for personal cleansing; products for treating human skin, including application of creams, lotions, and other topically applied products; products for shaving, rinse, rinse in shampoo; hair styling agents such as pomade, hair tonic, hair gel, hair cream and hair mousse; hair growing agents; hair coloring agents, etc.); and bath agents (e.g., powder bath additives, solid foaming bath additives, bath oils, bubble bath aroma generators, bath salts, etc.); hair removal products (e.g., products for hair removal including depilatory creams, sugar pastes or gels, waxes); writing products (e.g., pens, crayons, paints, pencils, paper, origami, seals, etc.); products for play (e.g., balls, beanbags, cards, tops, dolls, building blocks, etc.); flavored products (e.g., confections, beverages, snacks, prepared meals, over-the-counter medications, gum, etc.); pharmaceuticals (e.g., plasters, ointments, suppositories, tablets, liquid medicines, capsules, granules, pharmacologically active molecular and/or biological entities; their use in the treatment and/or prevention of diseases and/or alleviation of symptoms in humans and/or animals, and formulations, regimens, kits and/or routes of delivering such entities to subjects in need of treatment and/or prevention and/or alleviation, etc.); health care products (e.g., oral health care products, including any composition for use with any soft and/or hard tissue of the oral cavity or conditions associated therewith (e.g., anti-cavities compositions, anti-plaque chewing gum compositions, breath compositions, dentrifices, denture compositions, lozenges, rinses, and tooth whitening compositions), cleaning devices, floss and flossing devices and toothbrushes; over-the-counter health care including cough and cold remedies and treatments for other respiratory conditions, pain relievers whether topical, oral, or otherwise, gastrointestinal remedies including any composition suitable for the alleviation of gastrointestinal conditions such as heartburn, upset stomach, diarrhea, and irritable bowel syndrome, and nutrient supplementation such as calcium or fiber supplementation, etc.); and foods and drinks or beverage (e.g., confectioneries consisting of gum, candy, snack such as potato crisps, baked sweets such as cookie and biscuit; drinks including refreshing drinks such as flavored tea, herb tea, juice, soda and powdered drink, fancy drinks such as tea and coffee, and milk drinks; frozen desserts such as ice cream, sherbet, mousse and frozen yogurt; desserts such as custard pudding, jelly, bavarois, yogurt and cream; cooked foods such as soup, curry and stew; seasonings such as condensed soup for noodles, dressing and mayonnaise; bakery products such as bread and donuts; daily products such as butter cream and margarine; fish paste products; etc.). In certain embodiments, the disclosed subject matter provides for use of the fragrance compounds and compositions described herein in a consumer product as described herein.

A broad range of concentrations and/or amounts of the fragrance composition can be employed in a consumer product. In certain embodiments of the present disclosure, the fragrance composition is admixed with a consumer product wherein the composition is present in an amount from about 0.0001 to about 90% weight/weight (w/w), or from about 0.001 to about 75% w/w, or from about 1 to about 50% w/w, or from about 5 to about 25% w/w, or from about 10 to about 15% w/w, and values in between.

In certain embodiments, the fragrance composition admixed with the consumer product comprises 2-methoxy-2-methylheptane, 7-methoxy-2,4-dimethyloct-2-ene, 7-methoxy-2,4,7-trimethyloct-2-ene, 7-(allyloxy)-2,4-dimethyloct-2-ene, 7-methoxy-2,4-dimethyloctane, 4-(allyloxy)-2,6-dimethylheptane, 2,6-dimethyl-4-((2-methylallyl)oxy)heptane, 4-methoxy-2,6-dimethylheptane, 2-methyl-4-((2-methylallyl)oxy)pentane, 2-(allyloxy)-4-methylpentane, 2-methyl-4-((3-methylbut-2-en-1-yl)oxy)pentane, or an isomer, stereoisomer, diastereoisomer, or enantiomer thereof, or a combination thereof. In particular embodiments, the fragrance composition admixed with the consumer product comprises 2-methoxy-2-methylheptane.

In certain embodiments, the consumer product base additionally includes one or more bases, solvents, and combinations thereof.

For example and not limitation, bases can include, but are not limited to, essential oils, lactones, aldehydes, alcohols, ketones, nitriles, esters, amides, oximes, and other fragrant compounds and perfuming co-ingredients.

For further example and not limitation, the solvents can include, but are not limited to, diproplyene glycol, propylene glycol, dieth-phthalate (DEP), diisononyl phthalate (DINP), benzyl benzoate, benzyl alcohol, iso propyl myristate (IPM), isopropyl palmitate (IPP/Deltyl Prime), butyl stearate, dioctyl adipate, triethyl citrate, methyl hydrogenated rosinate (CAS No. 8050-15-5), terpenes (e.g., Glidsol 100), paraffinic naphthenic solvent (e.g., LPA-170 Solvent), isoalkanes (e.g., Soltrol 170 Isoparaffin), isoparaffins, isooctadecanol, (e.g., Tego Alkanol 66), phenoxyethanol, diethylene glycol monoethyl ether (Carbitol low gravity), glycol ether (Methyl Carbitol), Dipropylene Glycol Methyl Ether (e.g., Dowanol DPM), Dipropylene Glycol Methyl Ether Acetate (e.g., Dowanol DPMA), Propylene glycol methyl ether (e.g., Dowanol PM Glycol Ether), Tripropylene Glycol Methyl Ether, Diisoheptyl Phthalate (e.g., Jayflex® 77 available from Exxon), deionized or distilled water, specially denatured ethyl alcohol (e.g., SDA 40B), Dimethyl Adipate/Dimethyl Glutarate (e.g., DBE®-LVP Esters available from FLEXISOLV®), Racemic mixture (+/−)-2,2-dimethyl-4-hydroxymethyl-1,3-dioxolane (e.g., Augo Clean Multi Solvent), Alcohol 40B Anhydrous 200 Proof, alcohol SDA 40B 190 Proof, Triacetin, 3-Methoxy-3-methyl-1-butanol (Solfit), Benzyl Laurate, Tripropylene Glycol Methyl Ether (e.g., Dowanol TPM), Dipropylene glycol n-butyl ether (e.g., Dowanol DPNB), Dimethyl siloxane, trimethylsiloxy-terminated (e.g., Dowanol Corning 200 Fluid), Caprylic/Capric Triglycerides (e.g., Neobee M-5), propylene glycol and glyceryl oleate (e.g., Arlacel 186), Uniceth-IC20L (e.g., Arlasolve 200 L), propanediol, 1, 3, Butyl Cellosolve, Hexylene glycol, Glycerine, N Methyl Stearate, Isopropyl alcohol, 2-Methyl-1,3-propanediol (e.g., MP Diol Glycol), Diethyl Citrate, Triethyl Acetyl Citrate, Isopentyldiacetate (IPD-AC, Dimethyl 2-methylpentanedioate (e.g., Rhodiasolv Iris), medium chain triglicyrides (MTC), terpene hydrocarbons (e.g., Dipentene 5100, DL-limonene (e.g., Dipentene 122), 3,5,5-trimethylhexyl acetate, Diethyl Malonate, Limonene (e.g., Unitene D), cyclohexyl acetate, para-tertiary-butyl (e.g., Vertenex), Ethyl Acetate, Diethyl Succinate, and combinations thereof.

EXAMPLES

The presently disclosed subject matter will be better understood by reference to the following Examples, which are provided as exemplary of the disclosed subject matter, and not by way of limitation.

Example 1: Preparation of 2-hydroxy-2-methylheptane from ethyl caproate

To an oven-dried 2 L three-neck round bottom flask equipped with a condenser, an addition funnel, and an inlet adapter was charged 800 ml of a 3M solution (2.4 mol) of methylmagnesium bromide in diethylether via cannula under a nitrogen atmosphere. To the addition funnel was added a solution of 150 g (1.04 mol) of ethyl caproate in 100 mL of anhydrous ether. The round bottom was immersed into an ice bath and the solution in the addition funnel was added dropwise over a period of 2 hours. After the addition was complete, the ice bath was removed and the solution was allowed to stir for an additional 4 hours until the reaction was complete. The round bottom was immersed into an ice bath once again and the reaction quenched by dropwise addition of 1N HCl until the evolution of gas ceased. At this point 1N HCl was added at a faster rate until all solids dissolved and the organic layer became clear and yellow. The mixture was transferred to a separatory funnel and the bottom aqueous layer was removed. The organic layer was then washed with 3×500 ml of 1N HCl. The aqueous washes were then combined and reextracted with 500 ml of diethylether. The combined organic layers were then washed with water and brine and the solvent carefully removed on a rotary evaporator to afford 127.85 g of crude 2-hydroxy-2-methylheptane as a yellow oil.

Dehydration of 2-hydroxy-2-methylheptane

The crude product described above was transferred to a round bottom flask equipped with a simple distillation setup. To facilitate dehydration, a drop of sulfuric acid was added to the crude product and the mixture was heated to 160° C. The product that distills over into the receiver was a mixture of 2-methyl-1-heptene, 2-methyl-2-heptene, and water, which settled out into a bottom layer. After the distillation was complete, the distillate was placed into a separatory funnel and the bottom water layer was removed. The olefin mix was then dried over anhydrous magnesium sulfate to afford 98.64 g of product which was used in the next step without further purification.

Methoxylation of 2-methyl-1(2)-heptene to 2-methoxy-2-methylheptane

To a 1 L two-neck round bottom flask equipped with an addition funnel and a condenser with a nitrogen gas inlet, 40 mL of concentrated sulfuric acid and 250 mL of anhydrous methanol were added and the resulting solution was heated to 35° C. and allowed to stir for 15 minutes. To the addition funnel was added 98.64 g (0.88 mol) of the mixture of 2-methyl-1-heptene and 2-methyl-2-heptene from the previous step. This solution was added drop-wise to the reaction over the course of 1 hour and the resulting mixture was stirred at 35° C. for an additional 6 hours until the reaction was complete. The reaction mixture was then transferred to a separatory funnel and allowed to settle. The top organic layer was separated and the bottom layer extracted with 3×250 ml of diethyl ether. These combined ether extracts were added to the original organic layer which was dried over anhydrous magnesium sulfate. The solution was then concentrated carefully on a rotary evaporator to afford 96.11 g of crude product. The product was then fractionally distilled through a 1'×2" fractionating column filled with stainless steel packing to afford 63.97 g of pure 2-methoxy-2-methylheptane. The overall yield of the process is 43% based on the starting ethyl caproate (b.p. 38-41° C. @ 35 Torr).

$^1$HNMR (500 MHz, CDCl$_3$) δ: 0.86 (t, 3H), 1.10 (s, 6H), 1.20-1.30 (m, 6H), 1.42 (dd, 2H), 3.14 (s, 3H).

The compound of this Example has multi-faceted odor characteristics and does not fall into one category. It is spicy, fresh, green and fruity.

Example 2: Perfume Compositions and Shampoo Formulations with 2-methoxy-2-methylheptane A perfume composition with a wasabi lotus note was prepared from the compound of Example 1 (2-methoxy-2-methylheptane) to demonstrate its use in a shampoo. The formulation, with and without 2-methoxy-2-methylheptane, is provided in Table 1, below:

TABLE 1

| Component | Formulation without Example 1 (wt-%) | Formulation with Example 1 (wt-%) |
|---|---|---|
| Citrus compound(s) | 22.00 | 22.00 |
| Floral compound(s) | 31.40 | 31.40 |
| Fruity compound(s) | 3.46 | 3.46 |
| Gourmand compound(s) | 1.10 | 1.10 |
| Green compound(s) | 0.52 | 0.52 |
| Musk compound(s) | 20.00 | 20.00 |
| Spicy compound(s) | 0.20 | 0.20 |
| Woody compound(s) | 16.30 | 16.32 |
| Example 1 (2-methoxy-2-methylheptane) - Spicy, fresh, green, fruity | — | 5.00 |
| Solvent (Dipropylene glycol (DPG)) | 5.00 | — |
| Total | 100 | 100 |

The fragrance was used at 0.8% in a shampoo and a panel of five experts evaluated the samples.

The composition of this Example, using the compound of Example 1 ((2-methoxy-2-methylheptane) was found to have added natural fresh notes, particularly on top, opening up the fragrance overall, compared to the composition of this example without the compound of Example 1. The freshness comes from the green spiciness of the compound of Example 1, which gives the composition a more natural floral character.

Example 3: Bleach Stability Studies with 2-methoxy-2-methylheptane

A bleach stability test was performed on 2-methoxy-2-methylheptane in a market sample Clorox® bleach with a pH of 12.62 and an initial chlorine (NaOCl) percentage of 7.99%. Samples were dosed at 0.05%. The samples were stored at room temperature (RT) and 45° C. After 2 weeks and 4 weeks, the hedonics (i.e., the fragrance) was qualitatively evaluated. The amount of chlorine was determined (% NaOCl) to determine the amount of chlorine lost as compared to the initial percentage of 7.99% (% Loss). The results are provided in Table 2, below, where "Control" refers to Clorox® bleach alone and "Example 1" refers to Clorox® bleach dosed with 2-methoxy-2-methylheptane.

TABLE 2

|   |   |   | Control | Example 1 |
|---|---|---|---|---|
| 2 weeks | Hedonics | RT | OK | Good |
|   |   | 45° C. | OK | Good |
| 4 weeks | Hedonics | RT | OK | Good |
|   |   | 45° C. | OK | Good |
| 2 weeks | % NaOCl | RT | 7.94% | 7.91% |
|   |   | 45° C. | 7.46% | 7.39% |
| 4 weeks | % NaOCl | RT | 7.89% | 7.84% |
|   |   | 45° C. | 7.00% | 6.89% |
| 2 weeks | % Loss | RT | 0.63% | 1.00% |
|   |   | 45° C. | 6.63% | 7.51% |
| 4 weeks | % Loss | RT | 1.25% | 1.88% |
|   |   | 45° C. | 12.39% | 13.75% |

Example 4: Synthesis of 7-methoxy-2,4-dimethyloct-2-ene

A suspension of sodium hydride (0.85 g, 0.035 mol) in anhydrous tetrahydrofuran (40 mL) was prepared under an inert atmosphere. 5,7-Dimethyloct-6-en-2-ol (5.0 g, 0.032 mol) was then added dropwise over a period of 20 minutes during which time the temperature of the mixture was raised to 75° C. After stirring an additional 24 hours, iodomethane (4.55 g, 0.032 mol) was added and the mixture was stirred at 75° C. until analysis by gas chromatography showed no more starting alcohol was present. The mixture was cooled to room temperature and 100 mL of diethyl ether was then added. The resulting solution was washed with saturated sodium bicarbonate solution (2×75 mL) and brine (50 mL). The organic phase was separated and dried over anhydrous magnesium sulfate, filtered, and the solvent removed under reduced pressure. The crude product was purified by distillation to afford 4.79 g (88% yield) of a colorless oil (b.p. 35-38° C. @ 1 Torr).

$^1$H NMR (400 MHz, CDCl$_3$) δ: 0.88 (d, 3H), 1.07 (d, 3H), 1.27 (m, 2H), 1.34 (m, 2H), 1.58 (s, 3H), 1.65 (s, 3H), 2.26 (m, 1H), 3.23 (m, 1H), 3.29 (s, 3H), 4.86 (d, 1H)

Example 5: Synthesis of 7-methoxy-2,4,7-trimethyloct-2-ene

7-Methoxy-2,4,7-trimethyloct-2-ene was prepared using the same procedure as shown in Example 4 from iodomethane (4.17 g, 0.029 mol) and 2,5,7-trimethyloct-6-en-2-ol (5.0 g, 0.029 mol).

The crude product was purified by distillation to afford 4.22 g (78% yield) of a colorless oil (b.p. 60-62° C. @ 1.4 Torr).

$^1$H NMR (400 MHz, CDCl$_3$) δ: 0.90 (d, 3H), 1.09 (d, 6H), 1.28 (m, 2H), 1.38 (m, 2H), 1.57 (s, 3H), 1.65 (s, 3H), 2.23 (m, 1H), 3.14 (s, 3H), 4.85 (d, 1H)

Example 6: Synthesis of 7-(allyloxy)-2,4-dimethyloct-2-ene 7-(allyloxy)-2,4-dimethyloct-2-ene was prepared using the same procedure as shown in Example 4 from 3-bromoprop-1-ene (1.42 g, 0.012 mol) and 5,7-Dimethyloct-6-en-2-ol (2.0 g, 0.012 mol).

The crude product was purified by distillation to afford 1.96 g (85% yield) of a pale yellow oil (b.p. 46-49° C. @ 0.15 Torr).

$^1$H NMR (400 MHz, CDCl$_3$) δ: 0.89 (d, 3H), 1.13 (d, 3H), 1.30 (m, 2H), 1.47 (m, 2H), 1.57 (s, 3H), 1.66 (s, 3H), 2.27 (m, 1H), 3.38 (m 1H), 3.95 (dm, 2H), 4.84 (d, 1H), 5.13 (d, 1H), 5.24 (d, 1H), 5.89 (m, 1H)

Example 7: Synthesis of 7-methoxy-2,4-dimethyloctane

7-Methoxy-2,4-dimethyloctane was prepared using the same procedure as shown in Example 4 from iodomethane (2.30 g, 0.019 mol) and 5,7-dimethyloctan-2-ol (3.0 g, 0.019 mol).

The crude product was purified by distillation to afford 2.54 g (78% yield) of a colorless oil (b.p. 43-47° C. @ 1.5 Torr).

$^1$H NMR (400 MHz, CDCl$_3$) δ: 0.77 (d, 3H), 0.79 (d, 3H), 0.83 (d, 3H), 0.96 (m, 1H), 1.06 (m, 1H), 1.08 (d, 3H), 1.20-1.54 (m, 5H), 1.60 (m, 1H), 3.21 (dt, 1H), 3.28 (s, 3H)

Example 8: Synthesis of 4-(allyloxy)-2,6-dimethylheptane 4-(allyloxy)-2,6-dimethylheptane was prepared using the same procedure as shown in Example 4 from 3-bromoprop-1-ene (4.20 g, 0.035 mol) and 2,6-dimethylheptan-4-ol (5.0 g, 0.035 mol).

The crude product was purified by distillation to afford 4.48 g (70% yield) of a colorless oil (b.p. 70-73° C. @ 1 Torr).

$^1$H NMR (400 MHz, CDCl$_3$) δ: 0.79 (d, 6H), 0.82 (d, 6H), 1.18 (m, 2H), 1.39 (dd, 2H), 1.68 (dd, 2H), 3.37 (bt, 1H), 3.94 (d, 2H), 5.12 (d, 1H), 5.22 (d, 1H), 5.88 (m, 1H)

Example 9: Synthesis of 2,6-dimethyl-4-((2-methylallyl)oxy)heptane 2,6-dimethyl-4-((2-methylallyl)oxy)heptane was prepared using the same procedure as shown in Example 4 from 3-chloro-2-methylprop-1-ene (3.14 g, 0.035 mol) and 2,6-dimethylheptan-4-ol (5.0 g, 0.035 mol).

The crude product was purified by distillation to afford 5.29 g (77% yield) of a colorless oil (b.p. 74-75° C. @ 0.8 Torr).

$^1$H NMR (400 MHz, CDCl$_3$) δ: 0.79 (d, 6H), 0.81 (d, 6H), 1.19 (m, 2H), 1.44 (m, 2H), 1.68 (m, 2H), 1.72 (s, 3H), 3.36 (bt, 1H), 3.81 (s, 2H), 4.80 (s, 1H), 4.93 (s 1H)

Example 10: Synthesis of 2-methyl-4-((2-methylallyl)oxy)pentane 2-methyl-4-((2-methylallyl)oxy)pentane was prepared using the same procedure as shown in Example 4 from 3-chloro-2-methylprop-1-ene (2.22 g, 0.025 mol) and 4-methylpentan-2-ol (2.5 g, 0.025 mol).

The crude product was purified by distillation to afford 1.95 g (51% yield) of a colorless oil (b.p. 50-52° C. @ 19 Torr).

$^1$H NMR (400 MHz, CDCl$_3$) δ: 0.80 (d, 3H), 0.84 (d, 3H), 1.11 (d, 3H), 1.15 (m, 1H), 1.48 (m, 1H), 1.69 (s, 3H), 1.72 (m, 1H), 3.44 (m, 1H), 3.75 (d, 1H), 3.91 (d, 1H), 4.80 (s, 1H), 5.12 (s, 1H)

Example 11: Synthesis of 2-(allyloxy)-4-methylpentane 2-(allyloxy)-4-methylpentane was prepared using the same procedure as shown in Example 4 from 3-bromoprop-1-ene (2.96 g, 0.025 mol) and 4-methylpentan-2-ol (2.5 g, 0.025 mol).

The crude product was purified by distillation to afford 1.80 g (52% yield) of a colorless oil (b.p. 42-43° C. @ 30 Torr).

$^1$H NMR (400 MHz, CDCl$_3$) δ: 0.79 (d, 3H), 0.81 (d, 3H), 1.08 (d, 3H), 1.13 (m, 1H), 1.45 (m, 1H), 1.70 (m, 1H), 3.46 (m, 1H), 3.83 (m, 1H), 4.01 (m, 1H), 5.10 (d, 1H), 5.22 (d, 1H), 5.86 (m, 1H)

Example 12: Synthesis of 2-methyl-4-((3-methylbut-2-en-1-yl)oxy)pentane 2-methyl-4-((3-methylbut-2-en-1-yl)oxy)pentane was prepared using the same procedure as shown in Example 4 from 1-chloro-3-methylbut-2-ene (3.07 g, 0.029 mmol) and 4-methylpentan-2-ol (3.0 g, 0.029 mol).

The crude product was purified by distillation to afford 3.05 g (61% yield) of a colorless oil (b.p. 53-55° C. @ 5.5 Torr).

$^1$H NMR (400 MHz, CDCl$_3$) δ: 0.82 (d, 3H), 0.84 (d, 3H), 1.09 (d, 3H), 1.16 (m, 1H), 1.45 (m, 1H), 1.62 (s, 3H), 1.69 (s, 3H), 1.70 (m, 1H), 3.42 (m, 1H), 3.83 (m, 1H), 3.97 (m, 1H), 5.31 (bt, 1H)

Example 13: Fragrance Composition with 2-methoxy-2-methylheptane

A fragrance composition will be prepared from the compound of Example 1 (2-methoxy-2-methylheptane) for incorporation into a pomegranate rose dish soap. The formulation is provided in Table 3, below:

TABLE 3

| Component | wt-% |
|---|---|
| Citrus compound(s) | 8.2 |
| Floral compound(s) | 29.3 |
| Fruity compound(s) | 47.3 |
| Gourmand compound(s) | 1.0 |
| Green compound(s) | 7.0 |
| Green, fruity compound(s) | 2.2 |

TABLE 3-continued

| Component | wt-% |
|---|---|
| Example 1 (2-methoxy-2-methylheptane) - Spicy, fresh, green, fruity | 5.0 |
| Total | 100.0 |

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications publications product descriptions, and protocols are cited throughout this application the disclosures of which are incorporated herein by reference in their entireties for all purposes.

What is claimed is:

1. A fragrance composition comprising a fragrance compound selected from the group consisting of:
    2-methoxy-2-methylheptane;
    7-methoxy-2,4-dimethyloct-2-ene;
    7-methoxy-2,4,7-trimethyloct-2-ene;
    7-methoxy-2,4-dimethyloctane;
    4-methoxy-2,6-dimethylheptane;
    stereoisomers thereof; and
    combinations thereof; and
    further comprising an additional fragrance compound selected from a citrus compound, a floral compound, a fruity compound, a gourmand compound, a green compound, a musk compound, a spicy compound, a woody compound, and combinations thereof.

2. The fragrance composition of claim 1, wherein the fragrance compound is 2-methoxy-2-methylheptane.

3. The fragrance composition of claim 1, further comprising a solvent.

4. A method of modifying the odor properties of a fragrance composition by adding to the fragrance composition an olfactory effective quantity of a fragrance compound selected from the group consisting of:
    2-methoxy-2-methylheptane;
    7-methoxy-2,4-dimethyloct-2-ene;
    7-methoxy-2,4,7-trimethyloct-2-ene;
    7-methoxy-2,4-dimethyl octane;
    4-methoxy-2,6-dimethylheptane;
    stereoisomers thereof; and
    combinations thereof, and
    an additional fragrance compound selected from a citrus compound, a floral compound, a fruity compound, a gourmand compound, a green compound, a musk compound, a spicy compound, a woody compound, and combinations thereof.

5. The method of claim 4, wherein the fragrance compound is 2-methoxy-2-methylheptane.

6. A consumer product, comprising a consumer product base and a fragrance compound selected from the group consisting of:
2-methoxy-2-methylheptane;
7-methoxy-2,4-dimethyloct-2-ene;
7-methoxy-2,4,7-trimethyloct-2-ene;
7-methoxy-2,4-dimethyl octane;
4-methoxy-2,6-dimethylheptane;
stereoisomers thereof; and
combinations thereof, and
an additional fragrance compound selected from a citrus compound, a floral compound, a fruity compound, a gourmand compound, a green compound, a musk compound, a spicy compound, a woody compound, and combinations thereof.

7. The consumer product of claim 6, wherein the fragrance compound is 2-methoxy-2-methylheptane.

8. The consumer product of claim 6, wherein the consumer product is selected from a fine fragrance, a personal care product, a home care product, and an air care product.

9. The consumer product of claim 8, wherein the fine fragrance is selected from parfum, extrait de parfum, eau de parfum, millesime, parfum de toilette, eau de toilette, eau de cologne, body splash, after shave, body mists, and baby colognes.

10. The consumer product of claim 8, wherein the personal care product is selected from lotions, creams, moisturizers, body washes, hand soaps, shampoos, conditioners, and soaps.

11. The consumer product of claim 8, wherein the home care product is selected from fabric conditioner, fabric softener, laundry detergent, laundry additive, rinse additive, bleach, dryer sheets, perfume beads, car care products, dishwashing detergent, and hard surface cleaners.

12. The consumer product of claim 8, wherein the air care product is selected from a candle, aerosol, air freshener, liquid electric air freshener, fragrance diffuser, gel air freshener, plug-in air freshener, plug-in oil, and wax melt.

13. A method of modifying the odor properties of a consumer product by adding to a consumer product base an olfactory effective quantity of a fragrance compound selected from the group consisting of:
2-methoxy-2-methylheptane;
7-methoxy-2,4-dimethyloct-2-ene;
7-methoxy-2,4,7-trimethyloct-2-ene;
7-methoxy-2,4-dimethyl octane;
4-methoxy-2,6-dimethylheptane;
stereoisomers thereof; and
combinations thereof, and
an additional fragrance compound selected from a citrus compound, a floral compound, a fruity compound, a gourmand compound, a green compound, a musk compound, a spicy compound, a woody compound, and combinations thereof.

14. A method of manufacturing a consumer product, comprising:
admixing a fragrance compound selected from the group consisting of:
2-methoxy-2-methylheptane;
7-methoxy-2,4-dimethyloct-2-ene;
7-methoxy-2,4,7-trimethyloct-2-ene;
7-methoxy-2,4-dimethyl octane;
4-methoxy-2,6-dimethylheptane;
stereoisomers thereof; and
combinations thereof, and
an additional fragrance compound selected from a citrus compound, a floral compound, a fruity compound, a gourmand compound, a green compound, a musk compound, a spicy compound, a woody compound, and combinations thereof,
with a consumer product base.

15. The method of claim 14, wherein the fragrance compound is incorporated into a fragrance composition prior to admixing with the consumer product base.

16. A fragrance compound, selected from the group consisting of:
7-methoxy-2,4-dimethyloct-2-ene;
7-methoxy-2,4,7-trimethyloct-2-ene;
7-methoxy-2,4-dimethyl octane; and
stereoisomers thereof.

* * * * *